US00PP23621P2

(12) United States Plant Patent
Barends

(10) Patent No.: US PP23,621 P2
(45) Date of Patent: May 21, 2013

(54) ***PELARGONIUM* PLANT NAMED 'FIPELDANLAVIMP'**

(50) Latin Name: *Pelargonium peltatum*
Varietal Denomination: Fipeldanlavimp

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 13/317,162

(22) Filed: Oct. 11, 2011

(51) Int. Cl.
*A01H 5/00* (2006.01)

(52) U.S. Cl.
USPC ..... Plt./332

(58) Field of Classification Search ..... Plt./332
See application file for complete search history.

*Primary Examiner* — Susan McCormick Ewoldt
(74) *Attorney, Agent, or Firm* — C. A. Whealy

(57) ABSTRACT

A new and distinct cultivar of *Pelargonium* plant named 'Fipeldanlavimp', characterized by its upright to somewhat outwardly spreading plant habit; freely basal branching habit; early and freely flowering habit; semi-double light purple-colored flowers with red purple-colored venation; and good garden performance.

1 Drawing Sheet

Botanical designation: *Pelargonium peltatum.*
Cultivar denomination: 'FIPELDANLAVIMP'.

BACKGROUND OF THE INVENTION

The present invention relates to a new and distinct cultivar of *Pelargonium* plant, botanically known as *Pelargonium peltatum*, commercially referred to as Ivy Geranium, and hereinafter referred to by the name 'Fipeldanlavimp'.

The new *Pelargonium* plant is a product of a planned breeding program conducted by the Inventor in De Lier, The Netherlands. The objective of the breeding program is to create new freely-branching and freely-flowering *Pelargonium* plants with large flowers and attractive leaf and flower coloration.

The new *Pelargonium* plant originated from a cross-pollination made by the Inventor in De Lier, The Netherlands of a proprietary selection of *Pelargonium peltatum* identified as code number 60007, not patented, as the female, or seed, parent with a proprietary selection of *Pelargonium peltatum* identified as code number 88876, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands in March, 2007.

Asexual reproduction of the new *Pelargonium* plant by vegetative terminal cuttings in a controlled greenhouse environment in De Lier, The Netherlands since July, 2007 has shown that the unique features of this new *Pelargonium* plant are stable and reproduced true to type in successive generations.

SUMMARY OF THE INVENTION

Plants of the new *Pelargonium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Fipeldanlavimp'. These characteristics in combination distinguish 'Fipeldanlavimp' as a new and distinct *Pelargonium* plant:

1. Upright to somewhat outwardly spreading plant habit.
2. Freely basal branching habit.
3. Early and freely flowering habit.
4. Semi-double light purple-colored flowers with red purple-colored venation.
5. Good garden performance.

Plants of the new *Pelargonium* differ primarily from plants of the female parent selection in flower color as plants of the female parent selection have pink-colored flowers.

Plants of the new *Pelargonium* differ primarily from plants of the male parent selection in leaf color as leaves of plants of the male parent selection do not have a distinct zonation pattern.

Plants of the new *Pelargonium* can be compared to plants of *Pelargonium peltatum* 'Fipeldanlav', disclosed in U.S. Plant Pat. No. 21,259. In side-by-side comparisons conducted in De Lier, The Netherlands, plants of the new *Pelargonium* differed primarily from plants of 'Fipeldanlav' in flowering response as plants of the new *Pelargonium* flowered earlier than plants of 'Fipeldanlav'.

Plants of the new *Pelargonium* can also be compared to plants of *Pelargonium peltatum* 'Toscana Teske', not patented. In side-by-side comparisons conducted in De Lier, The Netherlands, plants of the new *Pelargonium* differed primarily from plants of 'Toscana Teske' in flower form as flowers of plants of the new *Pelargonium* had more petals and petaloids than plants of 'Toscana Teske'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant. The photograph comprises a side perspective view of a typical flowering plant of 'Fipeldanlavimp' grown in a container.

DETAILED BOTANICAL DESCRIPTION

The aforementioned photograph and following observations, measurements and values describe plants grown during the summer in 10.5-cm containers in a glass-covered greenhouse in De Lier, The Netherlands and under cultural conditions which closely approximate commercial *Pelargonium* production. During the production of the plants day temperatures ranged from 16° C. to 28° C. and night temperatures ranged from 14° C. to 18° C. Plants were ten weeks old when the photograph and the description were taken. In the detailed description, color references are made to The Royal Horticultural Society Colour Chart, 2007 Edition, except where general terms of ordinary dictionary significance are used.

Botanical classification: *Pelargonium peltatum* 'Fipeldanlavimp'.

Parentage:

*Female, or seed, parent*.—Proprietary selection of *Pelargonium peltatum* identified as code number 60007, not patented.

*Male or pollen parent*.—Proprietary selection of *Pelargonium peltatum* identified as code number 88876, not patented.

Propagation:

*Type*.—By vegetative terminal cuttings.

*Time to initiate roots, summer*.—About four days at temperatures of 22° C.

*Time to initiate roots, winter*.—About one week at temperatures of 22° C.

*Time to produce a rooted young plant, summer*.—About 16 days at temperatures of 22° C. to 30° C.

*Time to produce a rooted young plant, winter*.—About three weeks at temperatures of 20° C. to 25° C.

*Root description*.—Medium in thickness, fibrous; whitish grey in color.

*Rooting habit*.—Moderately freely branching, medium density.

Plant description:

*Plant habit*.—Upright to somewhat outwardly spreading plant habit; uniformly mounded; densely foliated.

*Growth and branching habit*.—Moderately vigorous growth habit; freely basal branching habit.

*Plant height, to top of umbels*.—About 21 cm to 23 cm.

*Plant height, to top of leaves*.—About 12 cm.

*Plant width*.—About 10 cm to 35 cm.

*Lateral branches*.—Length: About 15 cm to 23 cm. Diameter: About 4 mm to 5 mm. Internode length: About 3 cm to 4.5 cm. Texture: Pubescent. Strength: Moderately strong. Color: Close to 137C.

Foliage description:

*Arrangement*.—Alternate; simple.

*Length*.—About 4 cm to 4.5 cm.

*Width*.—About 7 cm to 9.5 cm.

*Shape*.—Roughly orbicular; palmately lobed.

*Apex*.—Acute.

*Base*.—Cordate.

*Margin*.—Entire; palmately lobed.

*Venation pattern*.—Palmate.

*Texture, upper surface*.—Smooth, glabrous.

*Texture, lower surface*.—Slightly pubescent; more dense along venation.

*Color*.—Developing and fully expanded leaves, upper surface: Close to N137B; venation, close to N137B. Developing and fully expanded leaves, lower surface: Close to 147B; venation, close to 146B. Zonation pattern, upper surface only: Location: Center of leaf. Width: About 8 mm to 10 mm. Color: Close to N79B, actual color will vary with light levels. Petiole: Length: About 3.5 cm. Diameter: About 2 mm to 3 mm. Texture, upper and lower surfaces: Pubescent.

Flower description:

*Flower arrangement*.—Semi-double flowers arranged in rounded hemispherical umbels arising from apical leaf axils; umbels displayed above the foliar plane on strong peduncles; flowers face upright to outwardly.

*Fragrance*.—None detected.

*Quantity of flowers*.—Freely flowering habit; about 18 to 22 flowers and flower buds per umbel and about ten umbels developing per plant.

*Flowering season*.—In The Netherlands, flowering is continuous from late spring until frost in the autumn; early flowering habit, plants begin flowering about six to eight weeks after planting.

*Flower longevity*.—Individual flowers last about 2 to 14 days on the plant; flowers persistent.

*Umbel height*.—About 4.5 cm.

*Umbel diameter*.—About 7 cm.

*Flower diameter*.—About 4.5 cm by 5 cm.

*Flower depth* (*height*).—About 1.5 cm.

*Flower buds*.—Length: About 9 mm to 15 mm. Diameter: About 5 mm to 8 mm. Shape: Globular to elliptic. Color: Close to 146A.

*Petals*.—Quantity per flower: About eight to ten. Length: About 2.2 cm to 2.5 cm. Width: About 1.9 cm to 2.3 cm. Shape: Spatulate to obovate. Apex: Obtuse. Base: Attenuate. Margin: Entire. Texture, upper and lower surfaces: Smooth, glabrous; velvety. Color: When opening and fully opened, upper surface: Close to 77C; towards the base, close to 59A; venation, close to 59A; color does not fade with development. When opening and fully opened, lower surface: Close to 75C; towards the base, N57A and 59A; at the base, close to NN155D; venation, close to 59A; color does not fade with development.

*Petaloids*.—Quantity per flower: If present, one to three. Length: About 1.8 cm. Width: About 7 mm. Shape: Irregularly obovate to oblanceolate. Apex: Obtuse. Base: Attenuate. Margin: Entire. Texture, upper and lower surfaces: Smooth, glabrous; velvety. When opening and fully opened, upper surface: Close to 77C; towards the base, close to 59A; venation, close to 59A; color does not fade with development. When opening and fully opened, lower surface: Close to 75C; towards the base, N57A and 59A; at the base, close to NN155D; venation, close to 59A; color does not fade with development.

*Sepals*.—Quantity per flower: Five arranged in a single whorl. Length: About 1 cm. Width: About 3 mm. Shape: Lanceolate to acicular. Apex: Acute. Base: Lobate to truncate. Margin: Entire. Texture, upper and lower surfaces: Densely pubescent. Color, upper surface: Close to N137C. Color, lower surface: Close to 146A.

*Peduncle* (*umbel stem*).—Length: About 10 cm. Diameter: About 3 mm to 4 mm. Strength: Strong. Angle:

Erect to about 30° C. from vertical. Texture: Pubescent. Color: Close to 146A.

*Pedicel* (*individual flower stem*).—Length: About 1.5 cm. Diameter: About 2 mm. Strength: Moderately strong. Angle: Erect to about 60° C. from vertical. Texture: Pubescent. Color: Close to 146B.

*Reproductive organs*.—Androecium: Stamen quantity per flower: About ten. Filament length: About 8 mm to 9 mm. Filament color: Close to 155A. Anther length: About 2 mm to 3 mm. Anther shape: Oblong. Anther color: Close to 39A. Pollen amount: Moderate. Pollen color: Close to 33B. Gynoecium: Pistil quantity per flower: One. Pistil length: About 1.2 cm to 1.4 cm. Stigma shape: Tapering; reflexed. Stigma color: Close to 64A. Style length: About 1 cm. Style color: Close to N74D. Ovary color: Close to 138D.

*Fruits and seeds*.—Fruit and seed development has not been observed on plants of the new *Pelargonium*.

Disease/pest resistance: Plants of the new *Pelargonium* have not been observed to be resistant to pathogens and pests common to *Pelargoniums*.

Garden performance: Plants of the new *Pelargonium* have been observed to have good garden performance and to tolerate rain, wind and temperatures ranging from about 1° C. to 35° C.

It is claimed:

1. A new and distinct *Pelargonium* plant named 'Fipeldanlavimp' as illustrated and described.

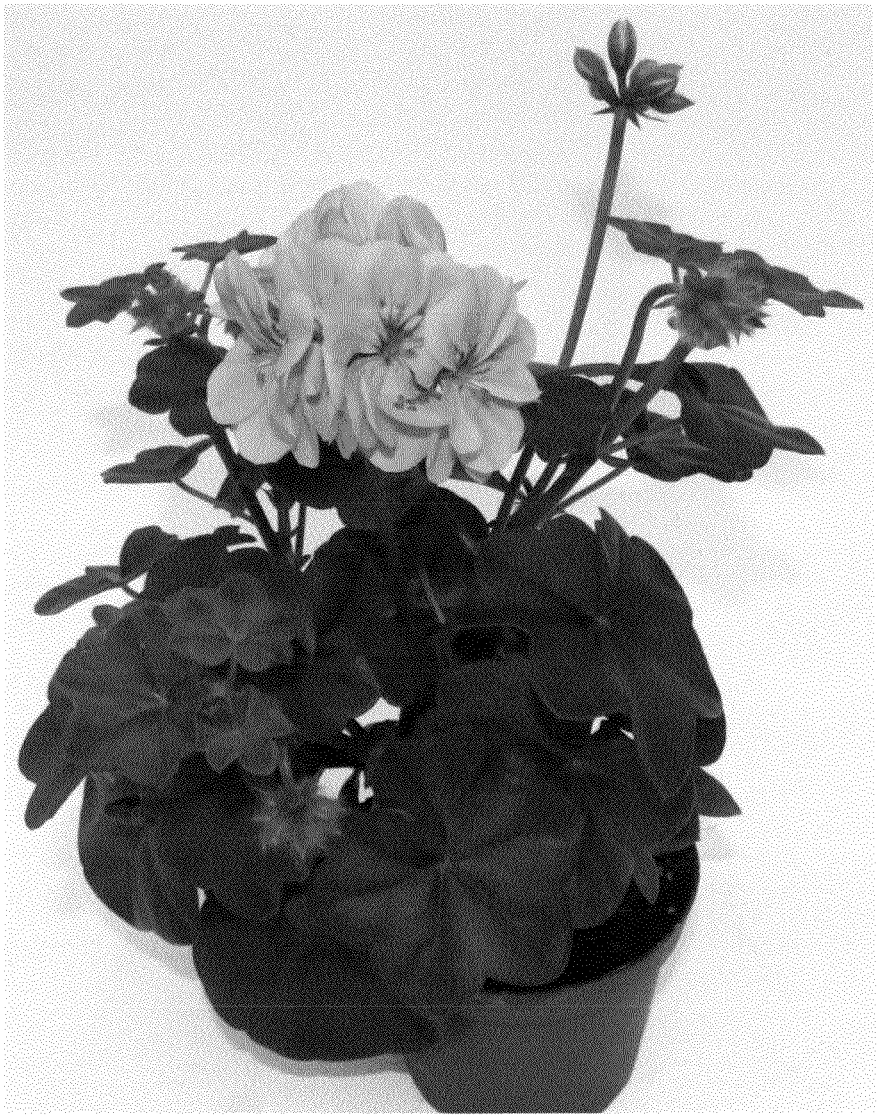

* * * * *